(12) United States Patent
Ludwig et al.

(10) Patent No.: US 8,894,690 B2
(45) Date of Patent: Nov. 25, 2014

(54) OFFSET CONNECTION BONE ANCHOR ASSEMBLY

(75) Inventors: Steven Ludwig, Baltimore, MD (US); William J. Frasier, New Bedford, MA (US); Michael Mahoney, Middletown, RI (US); Nicholas Pavento, Marlboro, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 959 days.

(21) Appl. No.: 11/897,571

(22) Filed: Aug. 31, 2007

(65) Prior Publication Data
US 2009/0062864 A1 Mar. 5, 2009

(51) Int. Cl.
*A61B 17/70* (2006.01)
*A61B 19/00* (2006.01)

(52) U.S. Cl.
CPC .......... *A61B 17/7041* (2013.01); *A61B 17/701* (2013.01); *A61B 2019/307* (2013.01); *A61B 17/705* (2013.01)
USPC ........................................................ 606/264

(58) Field of Classification Search
USPC ........ 606/246–279, 86 A; 411/166, 396, 401, 411/403
See application file for complete search history.

(56) References Cited

U.S. PATENT DOCUMENTS

| | | | |
|---|---|---|---|
| 4,653,481 A | 3/1987 | Howland et al. | |
| 5,030,220 A * | 7/1991 | Howland | 606/261 |
| 5,306,275 A | 4/1994 | Bryan | |
| 5,474,551 A | 12/1995 | Finn et al. | |
| 5,584,834 A | 12/1996 | Errico et al. | |
| 5,609,592 A | 3/1997 | Brumfield et al. | |
| 5,624,441 A | 4/1997 | Sherman et al. | |
| 5,688,275 A * | 11/1997 | Koros et al. | 606/264 |
| 5,810,817 A * | 9/1998 | Roussouly et al. | 606/250 |
| 5,984,922 A | 11/1999 | McKay | |
| 6,468,276 B1 | 10/2002 | McKay | |
| 6,562,038 B1 | 5/2003 | Morrison | |
| 6,626,906 B1 | 9/2003 | Young | |
| 6,726,692 B2 | 4/2004 | Bette et al. | |
| 6,770,075 B2 | 8/2004 | Howland | |
| 6,786,907 B2 * | 9/2004 | Lange | 606/250 |
| 6,964,665 B2 | 11/2005 | Thomas et al. | |

(Continued)

FOREIGN PATENT DOCUMENTS

| | | |
|---|---|---|
| EP | 1339337 B1 | 9/2003 |
| EP | 1405606 A2 | 4/2004 |

(Continued)

OTHER PUBLICATIONS

Ebara, Sohei et al., "A New System for the Anterior Restoration and Fixation of Thoracic Spinal Deformities Using an Endoscopic Approach," *Spine*, vol. 25(7):876-883 (2000).

*Primary Examiner* — Jan Christopher Merene
*Assistant Examiner* — Steven Cotroneo
(74) *Attorney, Agent, or Firm* — Nelson Mullins Riley & Scarborough LLP

(57) ABSTRACT

A bone anchor assembly for coupling an offset bone anchor with a previously inserted spinal fixation element and method of use is provided. Exemplary embodiments of a bone anchor assembly are particularly suited for use in a rod-first spinal surgical technique in which a bone anchor inserted into a patient vertebra may be separated from a previously inserted spinal fixation element by a separation distance.

12 Claims, 12 Drawing Sheets

(56) References Cited

U.S. PATENT DOCUMENTS

| | | | |
|---|---|---|---|
| RE39,035 E | 3/2006 | Finn et al. | |
| 7,166,108 B2 | 1/2007 | Mazda et al. | |
| 2002/0169450 A1* | 11/2002 | Lange | 606/61 |
| 2003/0045874 A1* | 3/2003 | Thomas, Jr. | 606/61 |
| 2003/0093078 A1* | 5/2003 | Ritland | 606/73 |
| 2004/0236330 A1 | 11/2004 | Purcell et al. | |
| 2006/0079899 A1* | 4/2006 | Ritland | 606/61 |
| 2006/0089651 A1 | 4/2006 | Trudeau et al. | |
| 2006/0111730 A1 | 5/2006 | Hay | |
| 2006/0155278 A1 | 7/2006 | Warnick | |
| 2006/0173456 A1 | 8/2006 | Hawkes et al. | |
| 2006/0264934 A1 | 11/2006 | Fallin | |
| 2006/0282074 A1 | 12/2006 | Renaud et al. | |

FOREIGN PATENT DOCUMENTS

| | | | |
|---|---|---|---|
| WO | WO-98/49961 A1 | 11/1998 | |
| WO | WO0152756 A1 * | 7/2001 | A61B 17/70 |
| WO | WO-2004/080318 A1 | 9/2004 | |
| WO | WO-2006/023514 A1 | 3/2006 | |
| WO | WO-2006/047742 A2 | 5/2006 | |
| WO | WO-2006/081375 A2 | 8/2006 | |

* cited by examiner

OFFSET CONNECTION BONE ANCHOR ASSEMBLY

FIELD OF INTEREST

The present invention relates to offset connection bone anchors and methods of use during orthopedic surgery. More particularly, the present invention relates to offset connection bone anchor assemblies for coupling a spinal fixation element with an offset bone anchor that is displaced from the spinal fixation element.

BACKGROUND

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g., a rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive elements and methods for implanting spinal fixation devices. For example, one such method, a rod-first method, includes inserting a spinal rod through a first incision and positioning the spinal rod along a patient's spinal column adjacent to one or more vertebra. After the spinal rod is inserted, a first bone anchor is inserted through the same incision or a remote incision, and each additional bone anchor is inserted through a separate incision along the spinal rod. After a bone anchor is inserted and anchored in bone, the bone anchor is coupled to the spinal rod. A rod-first method is a minimally invasive technique in which the bone anchors are inserted after the rod and adjacent to the rod, as opposed to a conventional surgical technique in which the bone anchors are inserted first; and then the rod is placed in rod-receiving elements lying over the heads of the bone anchors.

Unfortunately, in many instances, the bone anchors may not be inserted immediately adjacent to the spinal rod. Suitable vertebral sites for engagement of a bone anchor may not lie along a line. Using a conventional technique, the spinal rod can be bent to align the spinal rod with the bone anchors. Unfortunately, in percutaneous or minimally invasive procedures, it is more difficult to adjust a spinal rod using a technique such as bending to make contact between the spinal rod and the bone anchors, because the spinal rod is inserted and positioned in a patient before bone anchor insertion. Thus, there is a need for an offset connection bone anchor assembly configured to couple with a previously inserted spinal fixation element, such as a spinal rod, from which it is offset.

SUMMARY

In accordance with a first aspect, a bone anchor assembly is provided for connecting a previously inserted spinal fixation element with an offset bone anchor that is displaced from the spinal fixation element. The bone anchor assembly includes a bone anchor. The bone anchor includes a shaft and a seat element. The shaft has an engagement portion for engaging bone disposed at a distal end of the shaft, an extension portion disposed at a proximal end of the shaft and a central axis extending through the engagement portion of the shaft and the extension portion of the shaft. The extension portion has a length greater than a cross-sectional height of the spinal fixation element. The seat element is disposed between the engagement portion of the shaft and the extension portion of the shaft. The seat element has a profile flared in the direction of the proximal end of the shaft. The seat element also has a top surface configured to seat a previously inserted spinal fixation element and facing the proximal end of the shaft. The top surface of the seat element has a first seat distance. The first seat distance is a radial distance measured between the central axis of the bone anchor shaft and an outer edge of the top surface of the seat element measured in a first direction. According to aspects of an exemplary embodiment, the bone anchor assembly may also include a clamp element configured to clamp the spinal fixation element against the top surface of the seat element. The clamp element may include a securing element, or the bone anchor assembly may include a separate securing element for securing the spinal fixation element between the seat element and the clamp element.

According to other aspects of an exemplary embodiment, the first seat distance may be greater than or about equal to the sum of: the half a width of the spinal fixation element, the shaft radius measured at a distance equal to half the height of the spinal fixation element above the top surface of the seat element, and 2 mm. The first seat distance may be a maximum seat distance and may be larger than a distance between the central axis of the bone anchor shaft and an outer edge of the top surface of the seat element in a different direction. The seat element may have a maximum seat distance in more than one direction.

According to other aspects of an exemplary embodiment, the seat element may be affixed to the shaft of the bone anchor or the seat element may be integral with the shaft of the bone anchor. Alternately, the seat element may be rotatably coupled with the shaft of the bone anchor. The seat element may include a seat lock for fixing a position of the seat element relative to the shaft of the bone anchor. The bone anchor shaft may include a breakaway portion disposed at a proximal end of the shaft and configured to separate from the shaft.

In accordance with another aspect, a bone anchor assembly is provided for coupling a previously inserted spinal fixation element with an offset bone anchor that is displaced from the spinal fixation element. The method includes providing a bone anchor assembly. The bone anchor assembly includes a bone anchor. The bone anchor includes a shaft and a seat element. The shaft has an engagement portion for engaging bone disposed at a distal end of the shaft, an extension portion disposed at a proximal end of the shaft and a central axis extending through the engagement portion of the shaft and the extension portion of the shaft. The seat element is disposed between the engagement portion of the shaft and the extension portion of the shaft. The seat element has a profile flared toward the proximal end of the shaft. The seat element also has a top surface configured to seat a previously inserted spinal fixation element and facing the proximal end of the shaft. The top surface of the seat element has a first seat distance. The first seat distance, which is a maximum seat distance, is a radial distance between the central axis of the bone anchor shaft and an outer edge of the top surface of the seat element measured in a first direction. The bone anchor assembly also includes a clamp element configured to clamp the spinal fixation element against the top surface of the seat element. The bone anchor assembly may include a separate securing element. The bone anchor shaft may include a breakaway portion disposed at a proximal end of the shaft and configured to separate from the shaft.

The method also includes inserting the bone anchor into a patient vertebra at a location displaced from the spinal fixation element. Inserting the bone anchor may include receiving auditory and/or tactile feedback regarding the position of the seat element relative to the spinal fixation element. The method further includes rotating the seat element until a direction of the maximum seat distance is oriented toward the spinal fixation element. The method also includes seating the spinal fixation element on the top surface of the seat element by reducing a separation between the spinal fixation element and a central axis of the bone anchor. The method further includes inserting the clamp element along the extension portion of the bone anchor shaft and positioning the clamp element in contact with the spinal fixation element. According to aspects of an exemplary embodiment, the method may also include inserting and positioning the securing element to secure the spinal fixation element between the clamp element and the seat element. The method may further include separating the breakaway portion of the bone shaft and removing it from the patient.

In accordance with another aspect, a bone anchor assembly is provided for coupling a previously inserted first spinal fixation element and connected bone anchors with a previously inserted second spinal fixation element. The method includes providing a bone anchor assembly. The bone anchor assembly includes a bone anchor. The bone anchor includes a shaft and a seat element. The shaft has an engagement portion for engaging bone disposed at a distal end of the shaft, an extension portion disposed at a proximal end of the shaft and a central axis extending through the engagement portion of the shaft and the extension portion of the shaft. The seat element is disposed between the engagement portion of the shaft and the extension portion of the shaft. The seat element has a profile toward the proximal end of the shaft. The seat element also has a top surface configured to seat a previously inserted spinal fixation element and facing the proximal end of the shaft. The first seat distance is a radial distance between the central axis of the bone anchor shaft and an outer edge of the top surface of the seat element measured in a first direction. The bone anchor assembly also includes a double clamp element configured to clamp the spinal fixation element against the top surface of the seat element and configured to simultaneously clamp a different spinal fixation element against an opposite side of a top surface of the seat element. The bone anchor assembly may include a separate securing element. The bone anchor shaft may include a breakaway portion disposed at a proximal end of the shaft and configured to separate from the shaft.

The method also includes inserting the bone anchor into a patient vertebra at a location adjacent to the first spinal fixation element and the second spinal fixation element. Inserting the bone anchor may include receiving auditory and/or tactile feedback regarding the position of the seat element relative to the first spinal fixation element and/or the second spinal fixation element. The method further includes seating the first spinal fixation element on the top surface of the seat element by reducing a separation between the first spinal fixation element and a central axis of the bone anchor. The method also includes seating the second spinal fixation element on the top surface of the seat element opposite the first spinal fixation element by reducing a separation between the second spinal fixation element and a central axis of the bone anchor. The method further includes inserting the double clamp element along the extension portion of the bone anchor shaft and positioning the double clamp element to clamp the first spinal fixation element and the second spinal fixation element against the seat element. According to aspects of an exemplary embodiment, the method may also include inserting and positioning the securing element to secure the first spinal fixation element and the second spinal fixation element between the double clamp element and the seat element. The first spinal fixation element and the second spinal fixation element may be different types of spinal fixation elements. The first spinal fixation element may be substantially non-parallel with respect to the second spinal fixation element. The method may further include separating the breakaway portion of the bone anchor shaft and removing it from the patient.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Exemplary embodiments described herein concern a bone anchor assembly for connecting an offset bone anchor, such as a pedicle bone screw or an anchor bolt, with a previously inserted spinal fixation element and methods of use. Exemplary embodiments of a bone anchor assembly are particularly suited for use in a "rod-first" type spinal surgical technique in which a bone anchor that is inserted into a patient vertebra may be separated from a elongate spinal fixation element (SFE) by a separation distance. Exemplary embodiments of a bone anchor assembly are sized and dimensioned for insertion through a minimally invasive surgical access port, such as a cannula. Additionally, exemplary embodiments of a bone anchor assembly are configured for use in a "rod-first" type surgical technique in which a spinal fixation element is inserted and positioned in a patient before insertion of bone anchors, and in which the bone anchors are positioned adjacent to the spinal fixation element and not beneath the spinal fixation element.

As described herein, an offset bone anchor is a bone anchor that is inserted into a patient vertebra and anchored in bone after insertion of a spinal fixation element (hereinafter SFE), and that is separated from the previously inserted SFE by a separation distance. This separation distance is not an offset distance between a central axis of the SFE and a central axis of a bone anchor shaft, but is a separation distance measuring a "gap" distance between an outer surface of an extension portion of the bone anchor shaft and a closest point on the spinal fixation element. Ideally, exemplary embodiments of a spanning connector can couple an SFE and a bone anchor separated by a "gap" separation distance of at least 2 to 5 mm. An embodiment of a spanning connector may be required to couple a SFE and a bone anchor separated by a "gap" separation distance of as large as about 10 mm in the case of a patient with a spinal deformity.

Figure 1A:
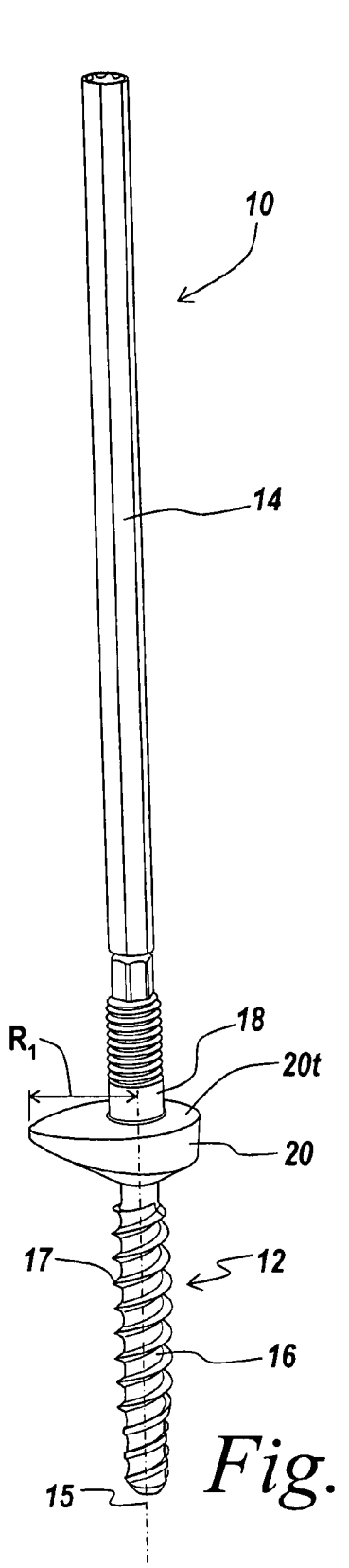
FIG. 1A illustrates an exemplary embodiment of a bone anchor assembly.
Figure 1B:
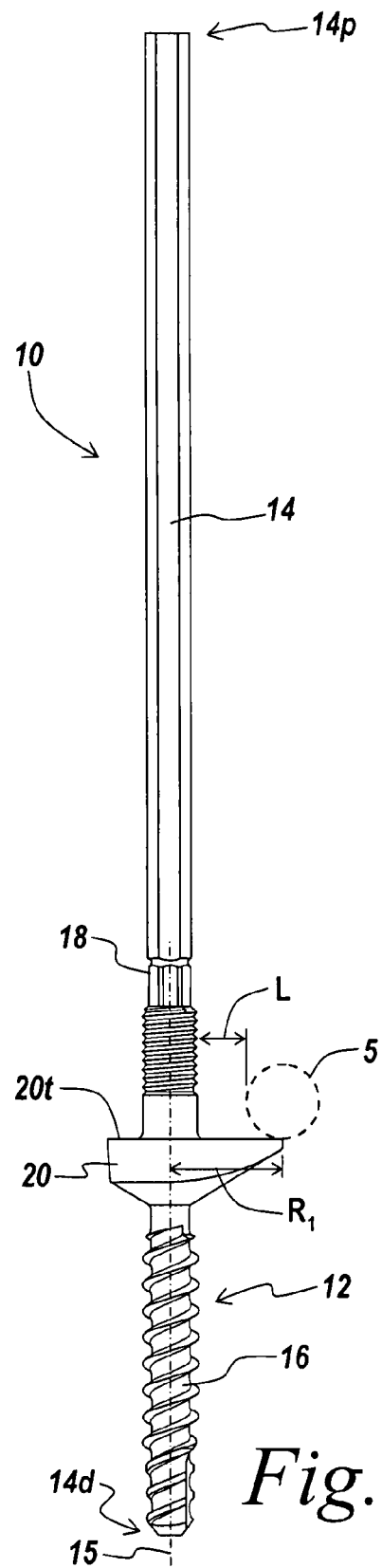
FIG. 1B illustrates a side view of the bone anchor assembly depicted in FIG. 1A.
Figure 1C:
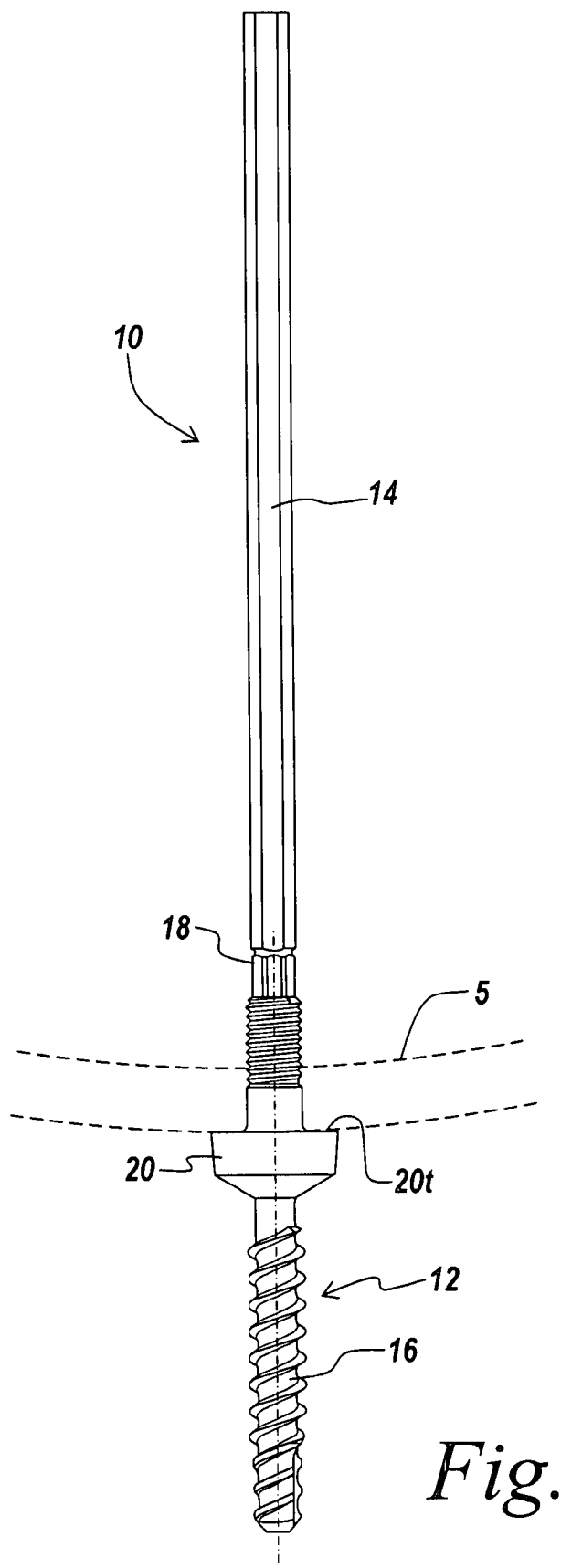
FIG. 1C illustrates a side view of the bone anchor assembly depicted in FIG. 1A.

FIGS. 1A, 1B and 1C illustrate an exemplary embodiment of a bone anchor assembly 10 for spanning a separation distance L to connect with a previously inserted spinal fixation element 5, such as a spinal rod. The bone anchor assembly 10 includes a bone anchor 12 with a shaft 14 and a seat element 20. The shaft 14 has an engagement portion 16 for engaging bone disposed at a distal end 14d of the shaft 14. The engagement portion 16 may include one or more external threads 17 for engaging bone, as depicted. The shaft 14 also has an extension portion 18 disposed at a proximal end 14p of the shaft 14. The shaft 14 also has a central axis 15 extending through the extension portion 18 of the shaft 14 and the engagement portion 16 of the shaft 14. The extension portion 18 of the shaft 14 has a length greater than a cross-sectional height of the SFE.

The bone anchor 12 also includes a seat element 20 that is disposed between the engagement portion 16 and the extension portion 18 of the shaft. The seat element 20 has a profile flared in the direction of the proximal end 14p of the shaft 14. A flared profile of the seat element 20 is illustrated by the side view of the bone anchor assembly 10 depicted in FIG. 1B and the front view of the bone anchor assembly 10 depicted in FIG. 1C. The seat element 20 has a top surface 20t configured to seat the previously inserted SFE 5 and facing the proximal end 14p of the shaft 14. The top surface 20t of the seat element 20 has a first distance $R_I$ measured from the central axis 15 of the bone anchor 12 to an outer edge of the top surface 20t of the seat element 20 in a first direction. The seat element 20 may be affixed to the bone anchor shaft 14 or the seat element 20 may be integral with the bone anchor shaft 14. Alternatively, the seat element 20 may be rotatably coupled with the bone anchor shaft 14 and may include a seat lock for fixing the position of the seat element 20 relative to the bone anchor shaft 14.

According to other aspects of the invention an exemplary seat element 20 may be pivotable, rotatable or conformable to adapt to seat a spinal fixation element with an "out of plane" orientation relative to the shaft 14. Embodiments of an adaptable seat element are discussed in detail in the related application DUQ-033 entitled "Adaptable Clamping Mechanism for Coupling a Spinal Fixation Element with a Bone Anchor," application Ser. No. 11/897,640, filed on Aug. 31, 2007.

The bone anchor 12 may be inserted by any appropriate method, ideally a minimally invasive method, including using a cannula, k-wire, etc. Techniques and instruments for minimally invasive insertion of a bone anchor and a connecting element are discussed in detail in the related applications: application DUQ-034 entitled "Minimally Invasive Guide System," application Ser. No. 11/897,642, filed on Aug. 31, 2007, and DUQ-037 entitled "Method and System for Securing a Rod to a Bone Anchor with a Connector," now U.S. Pat. No. 8,025,682, filed on Aug. 31, 2007.

A radial distance between the outer surface of the shaft 14 and the closest point of the SFE 5 is the gap separation distance L between the bone anchor 12 and the SFE 5. To properly seat a round SFE 5 with a SFE radius $R_R$ separated from the shaft 14 of the bone anchor 12 by a separation distance L, the first seat distance $R_I$, which is the distance between the central axis 15 of the shaft 14 and an outer edge of the top surface 20t of the seat element 20, should be about equal to or greater than the sum of: the half a width of the SFE $R_R$, which is the radius of the SFE for a SFE with a round cross-section, the separation distance L, and an outer radius $R_s$ of the shaft 14 measured at distance equal to half the height of the SFE (in this case $R_R$) above the top surface 20t of the seat element 20. Ideally, the exemplary bone anchor assembly 10 should span a separation distance of at least 2 mm. Thus, ideally, the first distance $R_I$ of the top surface 20t of the seat element 20 should be greater than or about equal to the sum of the SFE half width $R_R$, 2 mm and the bone anchor shaft radius $R_s$. A discussion of seating SFEs with non-circular cross-sections is presented below in the discussion of FIG. 4B.

According to aspects of an exemplary embodiment, the seat element 20 may be configured to provide tactile and/or auditory feedback to a surgeon regarding the relative position of the SFE 5 and the seat element 20 during insertion of the bone anchor 12 if the bone anchor 12 is implanted sufficiently close to the SFE 5 such that the seat element 20 and the SFE 5 contact each other during insertion. As the bone anchor 10 is inserted in the bone, the seat element 20 comes into contact with the SFE 5. The flared profile of the seat element 20 allows the seat element 20 to slide past the SFE 5 without becoming "caught" on the SFE 5. Additionally, contact with the flared profile of the seat element 20 causes the SFE 5 to be displaced away from the central axis 15 of the shaft 14 as the bone anchor 12 is inserted deeper. When the bone anchor 12 is inserted sufficiently deep that the SFE 5 lies above the top surface 20t of the seat element 20, the displaced SFE 5 suddenly "snaps" back to its original undisplaced position. The sudden change in SFE 5 position, and the sudden change in force on the bone anchor 12, may be felt by a surgeon through instruments connected to the bone anchor 12 and/or heard. After the SFE 5 "snaps" into place it is properly seated on the seat element 20.

According to other aspects of an exemplary embodiment, the top surface 20t of the seat element 20 may not be circular. The first distance $R_j$ may be a maximum distance and may be larger than a distance measured between the central axis 15 of the bone anchor shaft 14 and an outer edge of the top surface 20t of the seat element 20 in a different direction. The seat element 20 may have a maximum seat distance in more than one direction. If the top surface 20t of the seat element 20 is not circular, then a particular rotational orientation of the seat element 20 relative to the SFE 5, may be necessary for proper seating of the SFE 5. The distance $R_j$ of the top surface 20t of the seat element 20 should be directed toward the SFE 5. The method for adjusting the rotational orientation of the seat element 20 depends on the structure of the bone anchor 12. If the seat element 20 is rotatably coupled with the shaft 14, then the seat element 20 may be rotated to the proper orientation while the shaft 14 is stationary. If the seat element 20 is fixed to the shaft 14 or integral with the shaft 14, then the bone anchor shaft 14 must be rotated to change the orientation of the seat element 20. This may result in the seat element 20 being slightly higher or slightly lower than ideal because rotation to change the orientation of the seat element 20 also changes an insertion depth for the bone anchor 12. If the top surface 20t of the seat element 20 is substantially non-circular, the seat element 20 may not provide feedback to a surgeon in the manner discussed in the previous paragraph. The seat element 20 may only make intermittent contact with the SFE 5 during insertion if the seat element 20 is affixed to the shaft 14, or the SFE 5 may never "snap" into position if the seat element 20 is free to rotate with respect to the shaft 14.

Figure 2:
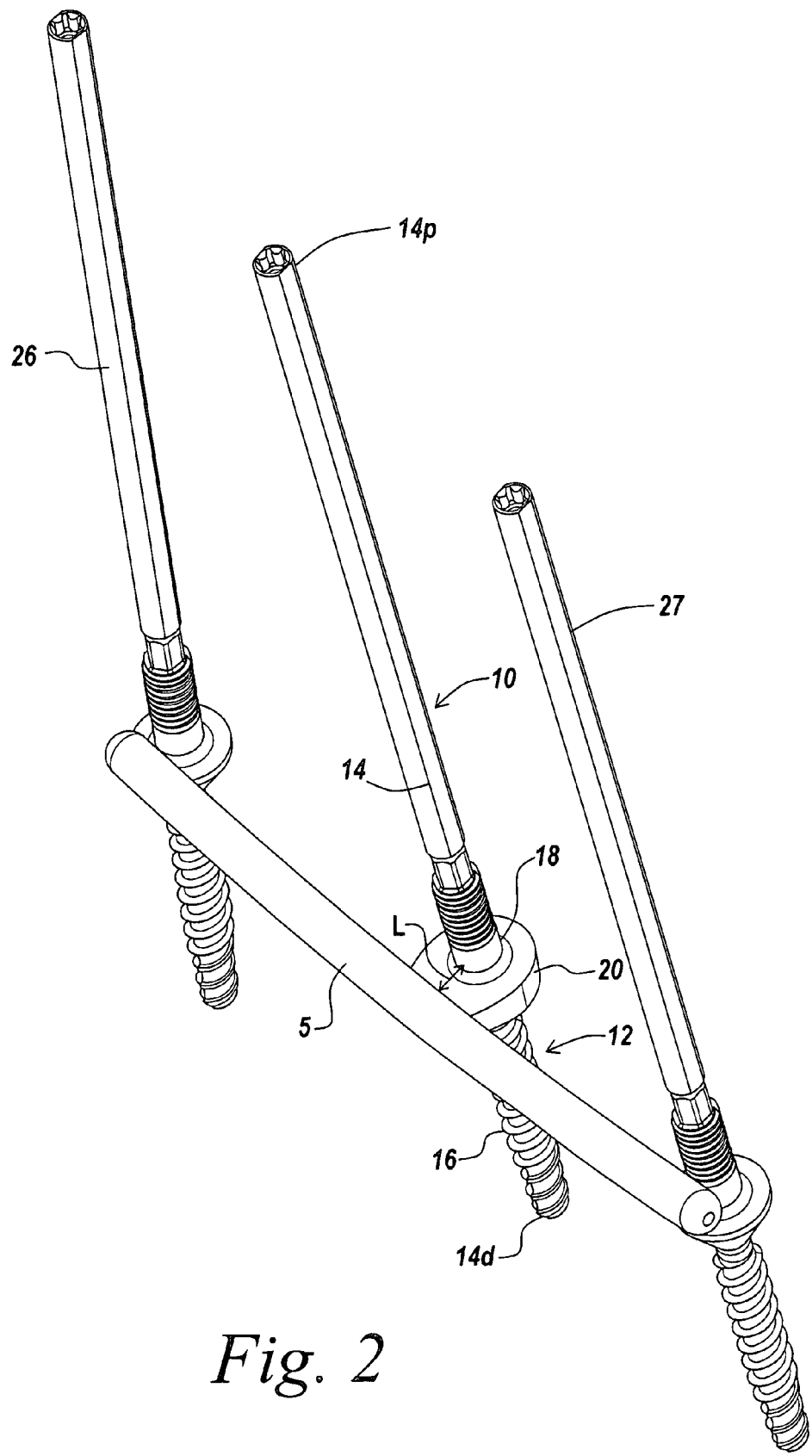
FIG. 2 illustrates a perspective view of the bone anchor assembly depicted in FIG. 1A in use.

FIG. 2 illustrates the bone anchor assembly 10 in use. In use, the SFE 5 is clamped against the seat elements with clamping elements and secured with securing elements. The clamping and securing elements are omitted from this figure to clearly display the seat elements. A first bone anchor 26 and a second bone anchor 27 support ends of a SFE 5. The bone anchor assembly 10 that supports the central portion of the SFE 5, lies out-of-line with the first bone anchor 26, the second bone anchor 27 and the SFE by the separation distance L.

Figure 3:
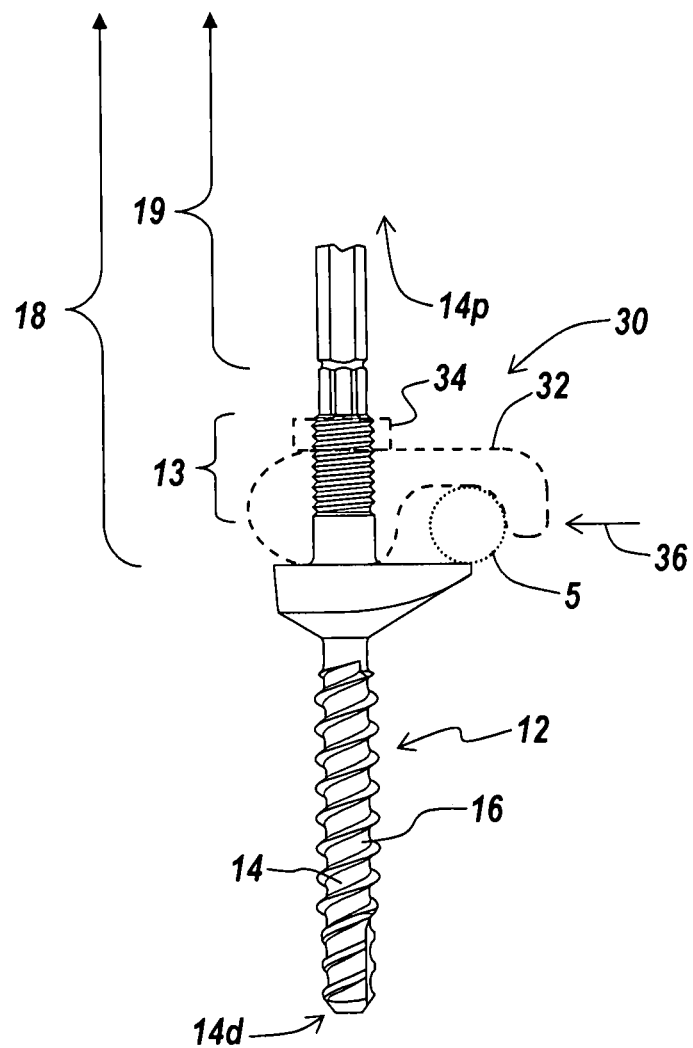
FIG. 3 illustrates an exemplary embodiment of a bone anchor assembly including a clamp element and a securing element.

FIG. 3 illustrates another exemplary embodiment of a bone anchor assembly 30 that includes a clamp element 32 and a securing element 34, according to aspects of an exemplary embodiment. The SFE 5 is seated on the seat element 20 before the clamp element 32 and the securing element 34 are positioned. The SFE 5 is seated on the seat element 20 by decreasing a separation between the SFE 5 and a central axis of the shaft as indicated by arrow 36. Engagement in a direction substantially perpendicular to the central axis of the shaft and substantially perpendicular to the central axis of the SFE, which will be called "engagement from the side", is particularly well suited for use with rod-first surgical techniques where the SFE is inserted before the bone anchors, unlike other engagement geometries such as in-line engagement or engagement from below. Although the bone anchor assembly 10 is configured to engage the spinal fixation element 5 "from the side", the bone anchor assembly 10 may instead be used to vertically engage the spinal fixation element 5.

After the SFE 5 is seated on the seat element 20, the clamp element 32 is inserted along the shaft 14 of the bone anchor 12 and positioned in contact with the SFE 5. The clamp element 32 may incorporate a securing element, or alternately, a separate securing element 34, such as a nut, may be inserted along the shaft 14 and used to exert force on the clamping element 32 to secure the SFE 5 between the clamp element 34 and the seat element 20. The clamp element 32, the securing element 34 and the bone anchor 12 may all be sized, dimensioned and configured for insertion into a patient through a minimally invasive surgical port such as a cannula. The extension portion 18 of the shaft may be sized and dimensioned to guide insertion of portions of the bone anchor assembly 10 into the patient. The extension portion 18 of the shaft may be include of a breakaway portion 19 disposed at a proximal end 14p of the shaft and a machine threaded portion 13. The securing element 34 may engage the threads in the machine threaded portion 13 of the shaft to secure the SFE 5. The breakaway portion 19 is designed to separate from the rest of the bone anchor 12 after the SFE 5 is secured to the bone anchor assembly 10. The breakaway portion 19 may be configured to separate from the rest of the bone anchor 12 when the securing element 34 is sufficiently tightened.

Figure 4A:
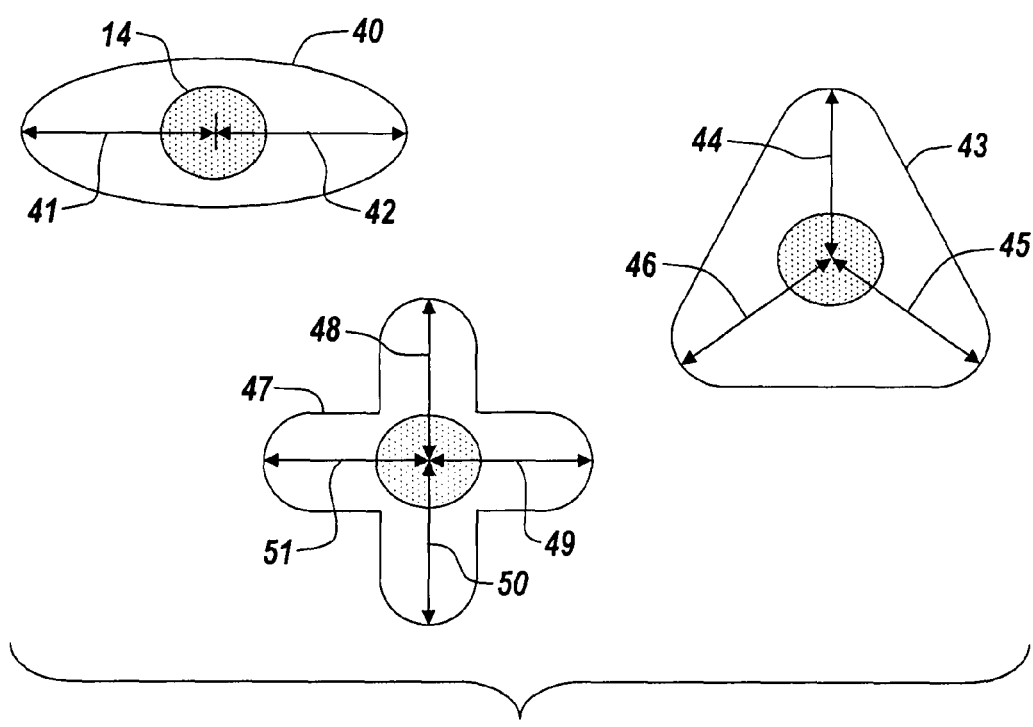
FIG. 4A illustrates top views of different shapes of seat elements, according to aspects of an exemplary embodiment.

FIG. 4A illustrates different shapes for a top surface 20t of the seat element 20 according to aspects of an exemplary embodiment. The shapes shown are intended to be illustrative and not exhaustive. As noted above, the top surface 20t of the seat element 20 may have a maximum distance in multiple directions. An elliptical seat element 40 has a maximum distance in two directions: direction 41 and direction 42. A triangular seat element 43 has a maximum distance in three directions: direction 44, direction 45 and direction 46. A cross-shaped seat element 47 has a maximum distance in four directions: direction 48, direction 49, direction 50 and direction 51. A top surface of the seat element may be asymmetric. One of ordinary skill in the art will appreciate that many other shapes of a top surface 20t of the seat element 20, although not specifically depicted herein, fall within the scope of the invention.

Figure 4B:
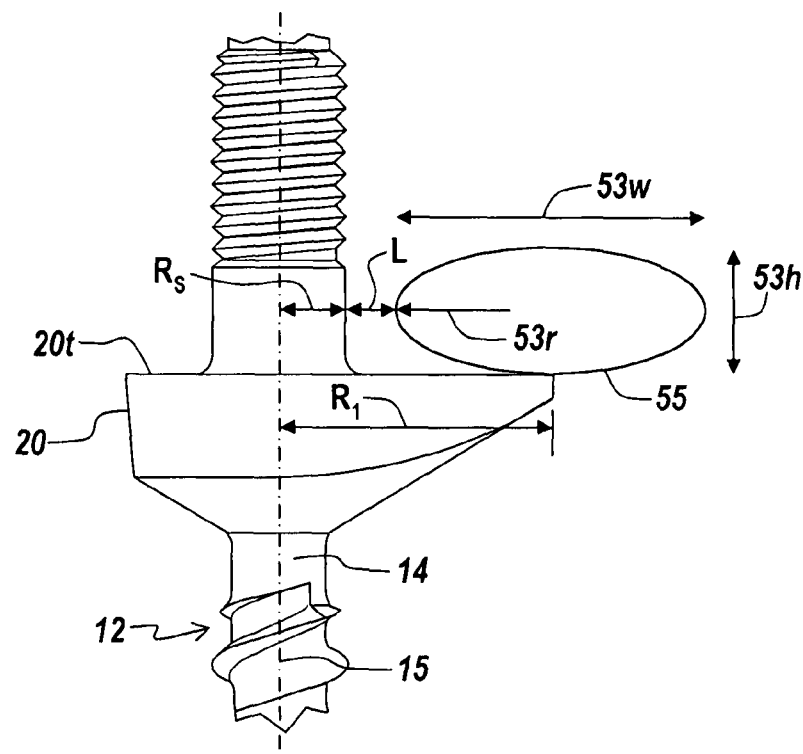
FIG. 4B illustrates cross-sectional shapes of different spinal fixation elements for use with exemplary embodiments of a bone anchor assembly.
Figure 4B:
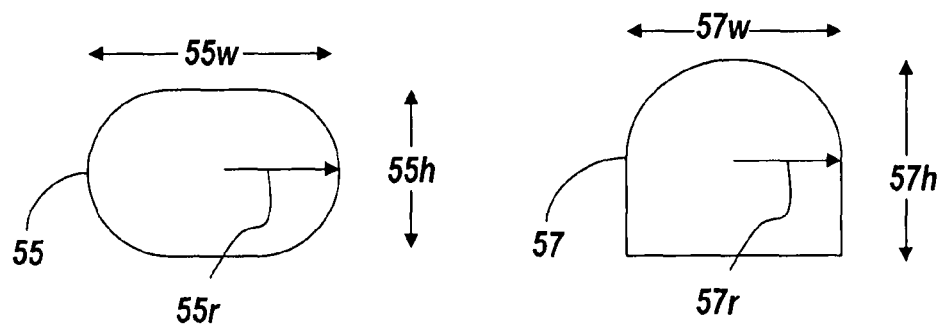
Figure 4B:
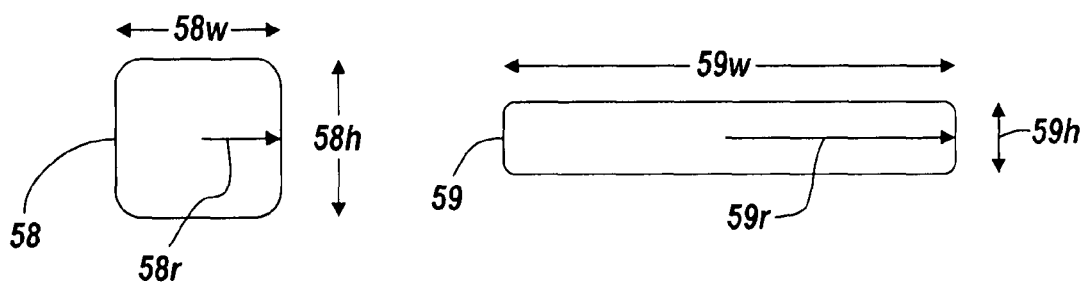

FIG. 4B illustrates cross-sectional shapes of different spinal fixation elements for use with exemplary embodiments of a bone anchor assembly. Although spinal fixation elements depicted in FIGS. 1B, 1C, 2 and 3 have substantially circular cross-sectional shapes, exemplary embodiments of a bone anchor assembly may be used with spinal fixation elements having different cross-sectional shapes. Spinal fixation element 53 has an elliptical cross-section with a distance 52r in a direction perpendicular to the axis 15 of the bone anchor 12, a height 52h and a width 52w. In this context, a "radius" of a spinal fixation element, such as element 52a, is defined as half the width of the spinal fixation element 52w measured at a height that is half the height 52h of the spinal fixation element. The width 52w is measured in a direction perpendicular to the bone anchor axis 15 and the height 52h is measured in a direction parallel to the bone anchor axis 15. Spinal fixation element 55 has a rounded elongate cross-sectional shape with a radius 55r, a height 55h and a width 55w. Spinal fixation element 57 has a half circle shape cross-section with a radius 57r, a height 57h and a width 57w. Spinal fixation element 58 has a substantially square cross-sectional shape with a radius 58r, a height 58h and a width 58w. Spinal fixation element 59 has a substantially rectangular cross-sectional shape with a radius 59r, a height 59h and a width 59w.

As discussed above with respect to FIGS. 1A, 1B and 1C, to properly seat a round SFE 5 with a SFE distance $R_R$ separated from the shaft 14 of the bone anchor 12 by a separation distance L, the first distance $R_1$ of the top surface 20t of the seat element 20 should be about equal to or greater than the sum of: the distance of the SFE $R_R$, the separation distance L, and an outer radius $R_s$ of the shaft 14 measured at distance equal to $R_R$ above the top surface 20t of the seat element 20. For an SFE that is not round, the above description must be modified. The modification will be described with respect to SFE 53. To properly seat a SFE that is not necessarily circular (for example elliptical SFE 53), separated from a shaft 14 of a bone anchor 12 by a separation distance L, the first distance $R_1$ of the top surface 20t of the seat element 20 should be about equal to or greater than the sum of: the half the width of the SFE (half of 52w) which is measured at a distance of half the height of the SFE (half of 52h) above the top surface 20t of the seat element 20. Ideally, the exemplary bone anchor assembly 10 should span a separation distance of at least 2 mm. Thus, ideally, the first distance $R_1$ of the top surface 20t of the seat element 20 should be greater than or about equal to the sum of: half the width of the SFE (half of 52w), the bone anchor shaft radius $R_s$ and 2 mm.

Figure 5:
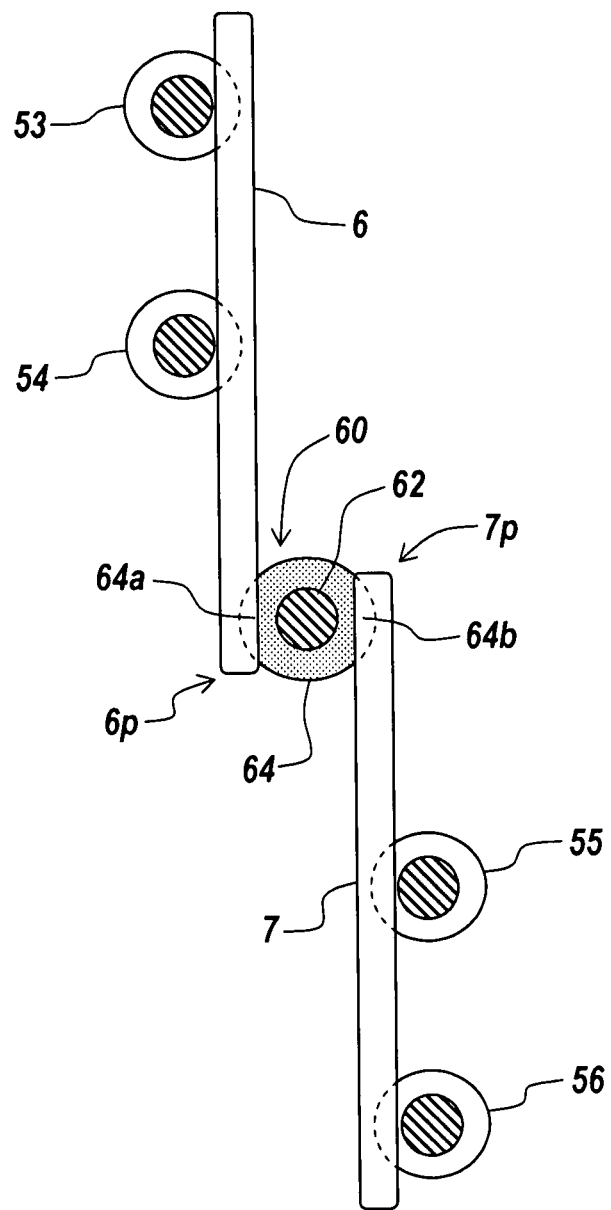
FIG. 5 illustrates a top view of another exemplary embodiment of a bone anchor assembly, including a double clamp, in use.

More than one bone anchor may be out-of-line with respect to some other bone anchors. Bone anchors may be inserted along one line (in-line) then jog to another parallel line (out-of-line) depending on patient anatomy and other factors affecting bone anchor placement. FIG. 5 illustrates a top view of an exemplary embodiment of a bone anchor assembly 60 in use coupling out-of-line bone anchors 55, 56 and a previously inserted out-of-line SFE 7 with in-line bone anchors 53, 54 and an in-line SFE 6. The bone anchor assembly 60 seats a proximal end 6p of the in-line SFE 6 on one portion of the seat element 64a and seats a proximal end 7p of the out-of-line SFE 7 on an opposite portion of the seat element 64b, (in this instance proximal refers to position relative to the bone anchor 12).

Figure 6:
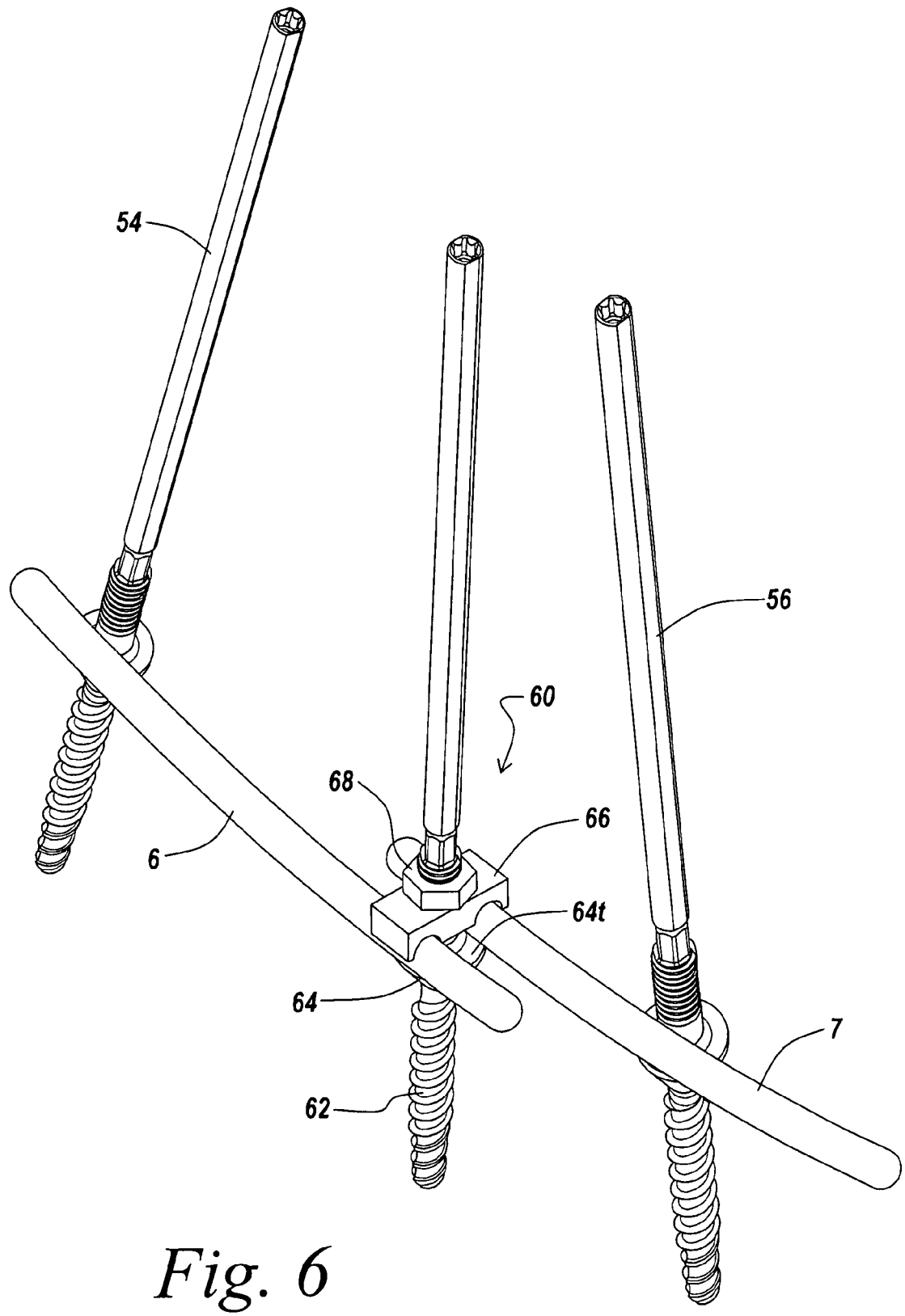
FIG. 6 illustrates a perspective view of the bone anchor assembly depicted in FIG. 5.

FIG. 6 illustrates a perspective view of the bone anchor assembly 60 in use. Only one in-line bone anchor 54 and one out-of line bone anchor 56 are depicted for clarity. The bone anchor assembly 60 includes a bone anchor 62 and a double clamp 66 for clamping the in-line SFE 6 and the out-of-line SFE 7 to the seat element 64. The double clamp element 66 secures both the in-line SFE 6 and the out-of-line SFE 7 to the bone anchor 62, coupling the in-line SFE 6 and the out-of-line SFE 7. The bone anchor assembly 60 may also include a securing element 68 to secure the in-line SFE 6 and the out-of-line SFE 7 between the double clamp 66 and the seat element 64. Ordinarily the bone anchors 54, 56 would also include clamp elements and securing elements which are omitted.

Figure 7:
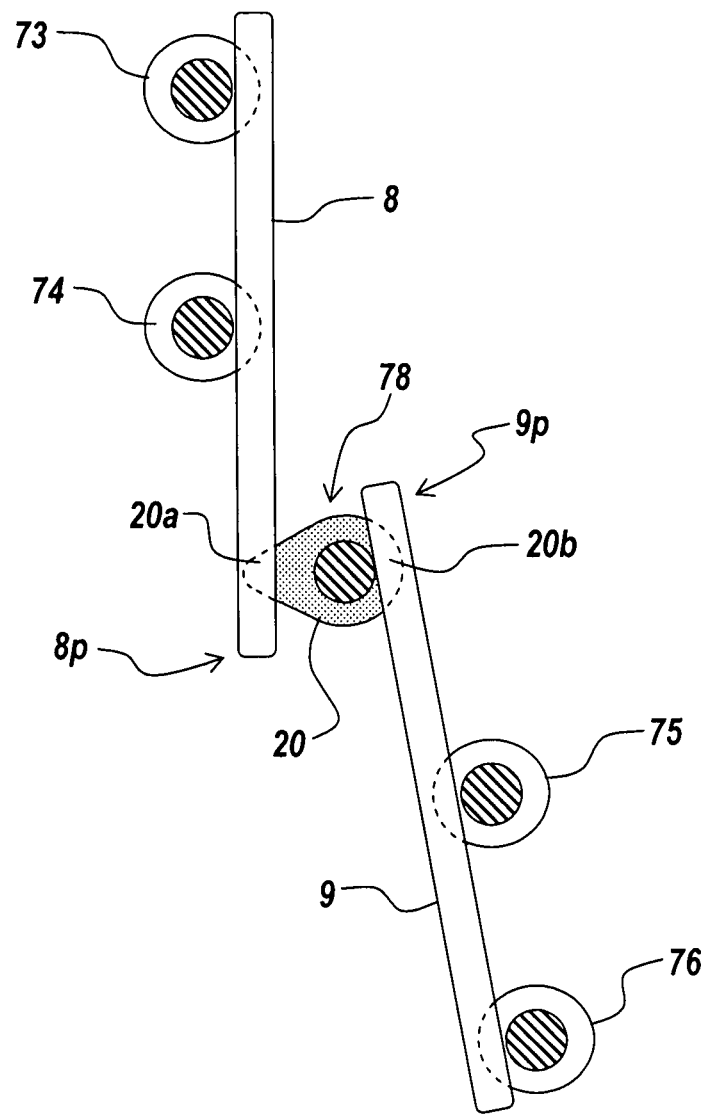
FIG. 7 illustrates a top view of an exemplary embodiment of a bone anchor assembly used to couple two non-parallel spinal fixation elements.

As illustrated in FIG. 7, out-of-line bone anchors 75, 76 implanted adjacent to an out-of-line SFE 9 may not be parallel to in-line bone anchors 73, 74 and an in-line SFE 8. Additionally, there may not be a suitable bone anchor site evenly spaced between the proximal end 8p of the in-line SFE 8 and the proximal end 9p of the out-of-line SFE 9. An exemplary bone anchor assembly 78 with the asymmetric seat element 20 (also see FIG. 1A for a perspective view of the asymmetric seat element 20) may be placed at suitable bone anchor site closer to the out-of-line SFE 9. The bone anchor assembly 78 seats the in-line SFE 8 on a first portion 20a of the seat element 20 that extends toward the in-line SFE 8 and seats the out-of-line SFE 9 on an opposite portion 20b of the seat element 20, coupling the out-of-line SFE 8 with the in-line SFE 9.

Figure 8:
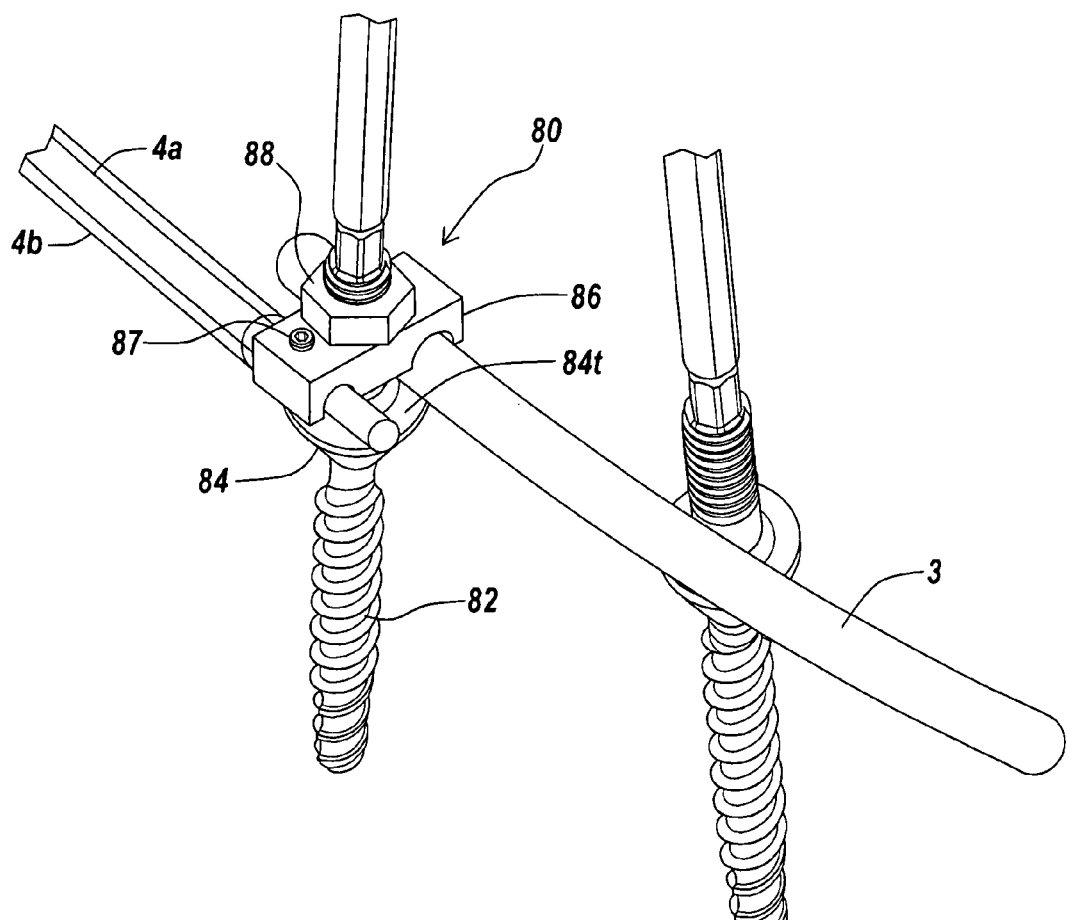
FIG. 8 illustrates a perspective view of an exemplary embodiment of a bone anchor assembly used to couple two different spinal fixation elements, a spinal rod and a dynamic spinal rod.

Another embodiment of the bone anchor assembly 80 may use a double clamp element that is a combination clamp element that couples different types of spinal fixation elements to a bone anchor, as illustrated in FIG. 8. The bone anchor assembly 80 includes a bone anchor 82 and a combination rod & cable clamp element 86 for clamping a cable 4a to a top surface 84t of the seat element 84 and clamping a rod 3 to an opposite portion of the top surface 84 of the seat element. The rod 3 may be displaced from the bone anchor 82. The cable 4a may be surrounded by a spacing sleeve 4b over portions of the cable 4a, the cable 4a and the spacing sleeve 4b forming a dynamic spinal rod. The combination rod & cable clamp element 86 may include a set screw 87 for further securing the cable 4a. Although the anchor assembly 80 depicts a combination rod & cable clamp element 86, one of ordinary skill in the art will appreciate that embodiments including double clamp elements that are combination clamp elements that couple many different types of spinal fixation elements to a bone anchor fall within the scope of the present invention.

A bone anchor assembly 80 with a double clamp element 66 or a combination clamp element 86 may be used to couple a newly inserted spinal fixation element and a previously inserted spinal fixation element with a bone anchor. The newly inserted spinal fixation element and the previously inserted spinal fixation element may be of a similar type or may be of different types. The previously inserted spinal fixation element may be part of an existing system that had been implanted in a previous surgery. For example, the dynamic spinal rod formed by the cable 4a and spacing sleeve 4b may have been a part of an existing spinal fixation system. The bone anchor assembly 80 may form part of an extension or an add-on to an existing system spinal fixation system. To add on to the existing spinal fixation element system, a bone anchor at an end of the previously inserted spinal fixation element (the cable 4a and spacing sleeve 46) may be removed and replaced with a bone anchor assembly 80 including a double clamp element 66 or a combination clamp element 86 suitable to clamp both the previously inserted spinal fixation element (the cable 4a and spacing sleeve 4b) and the newly inserted spinal fixation element (the rod 3).

Figure 9A:
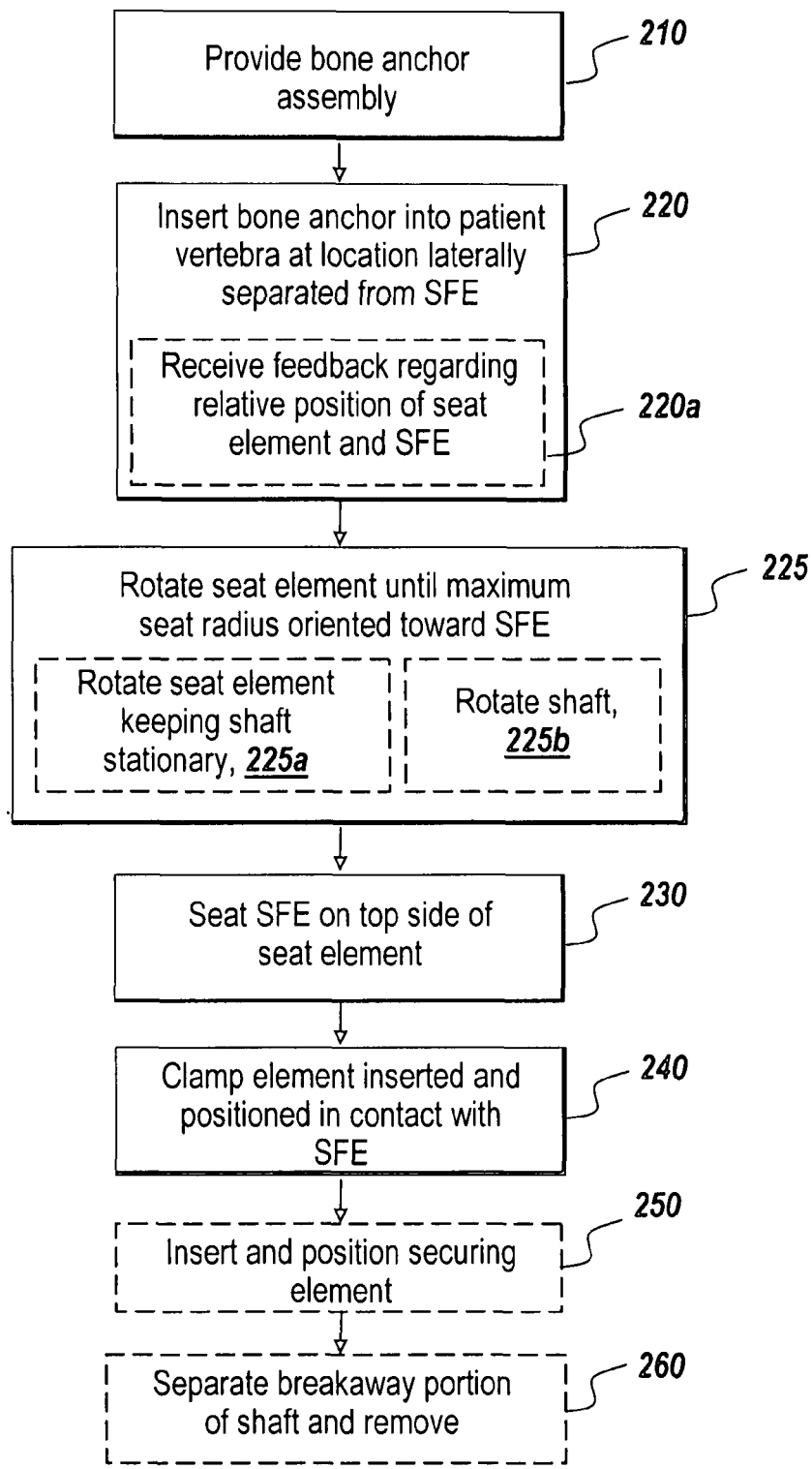
FIG. 9A is a flow diagram of an exemplary embodiment of a method for coupling an offset bone anchor with a previously inserted spinal fixation element.

FIG. 9A illustrates an exemplary embodiment of a method 200 for coupling an offset bone anchor with a previously inserted SFE. Solely for illustrative purposes, the method 200 will be described with respect to the bone anchor assembly 30 depicted in FIG. 3 which includes a clamp element 32 and a securing element 34. Initially, a bone anchor assembly 30 is provided (step 210). The bone anchor assembly 30 includes a bone anchor 12 with a shaft 14 and a seat element 20. The shaft 14 has an engagement portion 16 for engaging bone disposed at a distal end 14d of the shaft 14. The shaft 14 also has an extension portion 18 disposed at a proximal end 14p of the shaft 14. The shaft 14 also has a central axis 15 extending through the extension portion 18 and the engagement portion 16 of the shaft 14. The bone anchor 12 also includes a seat element 20 that is disposed between the engagement portion 16 of the shaft 14 and the extension portion 18 of the shaft. The seat element 20 has a profile flared in the direction of the proximal end 4p of the shaft 14. The seat element 20 has a top surface 20t configured to seat the previously inserted SFE 5 and facing the proximal end 14p of the shaft. The top surface 20t of the seat element 20 has a first distance $R_l$ measured from the central axis 15 of the bone anchor 12 to an outer edge of the top surface 20t of the seat element 20 in a first direction. The bone anchor assembly 30 may also include a clamp element 32 and a securing element 34.

The bone anchor 12 is inserted into a patient vertebra at a location separated from the SFE (step 220). As the bone anchor 12 is inserted, a surgeon may receive tactile and/or auditory feedback regarding a position of the seat element 20 relative to the SFE 5 (step 220a). If the first distance $R_l$ is a maximum seat distance, the seat element 20 may be rotated until the maximum seat distance is oriented toward the SFE 5 (225). Rotating the seat element 20 may include rotating the seat element 20 while holding the shaft 14 of the bone anchor 12 stationary (step 225a), or rotating the seat element 20 may include rotating the shaft 14 of the bone anchor 12 (step 225b). The SFE 5 is seated on the top surface 20t of the seat element 20 from the side (step 230). The clamp element 32 is inserted along the extension portion 18 of the shaft 14 of the bone anchor 12 and positioned in contact with the SFE 5 (step 240). The method may include inserting the securing element 34 along the extension portion 18 of the shaft 14 of the bone anchor 12 and tightening the securing element 34 against the clamp element 32 (step 250). The method may also include separating a breakaway portion 19 of the shaft 14 from the shaft 14 and removing the breakaway portion 19 from the patient (step 260).

Figure 9B:
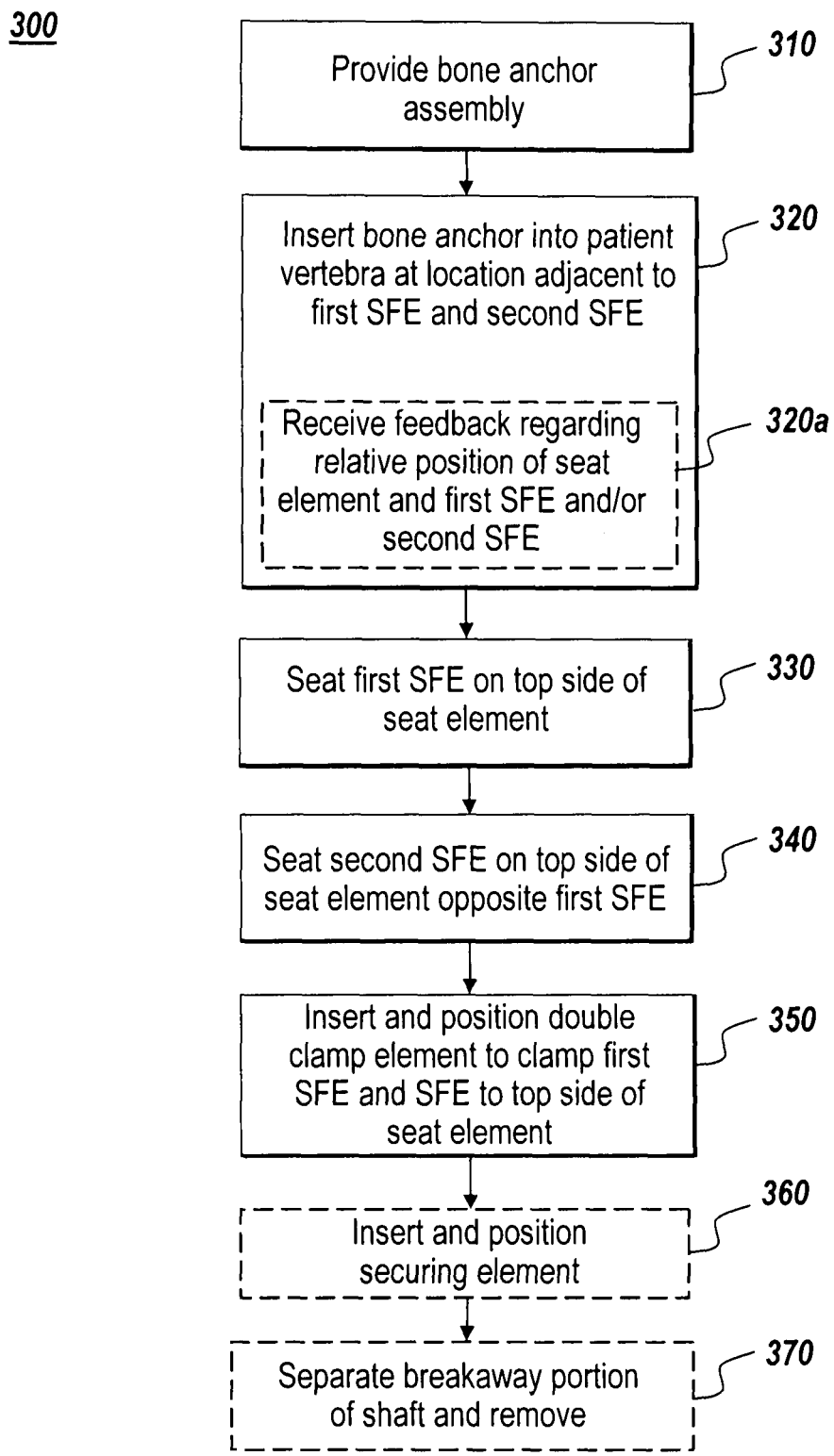
FIG. 9B is a flow diagram of an exemplary embodiment of a method for coupling two previously inserted spinal fixation elements.

FIG. 9B illustrates an exemplary embodiment of a method 300 for coupling a previously inserted out-of-line SFE, with in-line bone anchors coupled with a previously inserted in-line SFE. Initially, a bone anchor assembly 60 is provided (step 310). The bone anchor assembly 60 includes a bone anchor 12 with a shaft 14 and a seat element 20. The shaft 14 has an engagement portion 16 for engaging bone disposed at a distal end 14d of the shaft 14. The shaft 14 also has an extension portion 18 disposed at a proximal end 14p of the shaft 14. The shaft 14 also has a central axis 15 extending through the extension portion 18 and the engagement portion 16 of the shaft 14. The bone anchor 12 also includes a seat element 20 that is disposed between the engagement portion 16 of the shaft 14 and the extension portion 18 of the shaft. The seat element 20 has a profile flared in the direction of the proximal end 14p of the shaft 14. The seat element 20 has a top surface 20t configured to seat the previously inserted SFE 5 and facing the proximal and 14p of the shaft. The top surface 20t of the seat element 20 has a first distance $R_l$ measured from the central axis 15 of the bone anchor 12 to an outer edge of the top surface 20t of the seat element 20 in a first direction. The bone anchor assembly 60 also includes a double clamp element 66. The bone anchor assembly 60 may also include a securing element 68.

The bone anchor 12 is inserted into a patient vertebra at a location adjacent to a first SFE 8 and a second SFE 9 (step 320). As the bone anchor 12 is inserted, a surgeon may receive tactile and/or auditory feedback regarding a position of the seat element 20 relative to the first SFE 8 and/or the SFE 9 (step 320a). If the first distance $R_l$ is a maximum seat distance, the seat element 20 may be rotated until the maximum seat distance is oriented toward the first SFE 8 or the second SFE 9. The first SFE 8 is seated on the top surface 20t of the seat element 20 from the side (step 330). The second SFE 8 is seated on the top surface 20t of the seat element 20 opposite the first SFE (step 340). The double clamp element 66 is inserted along the extension portion 18 of the shaft 14 and positioned in contact with the first SFE 8 and the second SFE 9 to clamp the first SFE 8 and the second SFE 9 against the seat element 20 (step 350). A securing element may be inserted along the extension portion of the shaft 14 and used to secure the first SFE 8 and the second SFE 9 between the double clamp element 66 and the seat element 20 (step 360). The method may also include separating the breakaway portion 19 of the shaft 14 from the shaft 14 and removing the breakaway portion 19 from the patient (step 370).

While the figures depict exemplary embodiments of a bone anchor assembly for securing a SFE and methods of use, one of ordinary skill in the art will recognize that exemplary embodiments of a bone anchor assembly may couple with many different types of bone anchors, including but not limited to: bolts, screw, staples, anchors, hooks, etc. Additionally, exemplary embodiments of a bone anchor assembly may couple with many different types of spinal fixation elements, including but not limited to: plates, PDS (posterior dynamic stabilization) devices, cables, spinal rods such as solid rods, dynamic rods, etc.

One skilled in the art will appreciate further features and advantages of the invention based on the above-described embodiments. Accordingly, the invention is not to be limited by what has been particularly shown and described, except as indicated by the appended claims.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A bone anchor assembly for spanning a separation distance to connect laterally with a spinal fixation element, the assembly comprising:
  a bone anchor comprising:
    a shaft having:
      an engagement portion for engaging bone disposed at a distal end of the shaft,
      an extension portion disposed at a proximal end of the shaft, the extension portion having a length greater than a cross-sectional height of the spinal fixation element; and
      a central axis extending through the engagement portion of the shaft and the extension portion of the shaft; and
    a seat element disposed between the engagement portion of the shaft and the extension portion of the shaft, the seat element having:
      a profile flared in the direction of the proximal end of the shaft, wherein the profile is flared to provide a continuous angled surface extending from an outer edge of the seat to the shaft; and
        an elliptical top surface configured to be substantially flat to seat a previously inserted spinal fixation element separated from the shaft by the separation distance and facing the proximal end of the shaft, the top surface of the seat element having a first seat distance, in a first direction wherein the first seat distance is greater than or about equal to the sum of half of a cross-sectional width of the spinal fixation element, a radius of the shaft and 2 mm, wherein the first seat distance is the radial distance between the central axis of the bone anchor shaft and an outer edge of the top surface of the seat element in the first direction.

2. The bone anchor assembly of claim 1, wherein the first seat distance is a maximum seat distance and is larger than a distance between the central axis of the bone anchor shaft and an outer edge of the top surface of the seat element in a different direction.

3. The bone anchor assembly of claim 1, wherein the seat element has a maximum seat distance in more than one direction.

4. The bone anchor assembly of claim 1, wherein the seat element is affixed to the shaft of the bone anchor.

5. The bone anchor assembly of claim 1, wherein the seat element is integral with the shaft of the bone anchor.

6. The bone anchor assembly of claim 1, wherein the seat element is rotatably coupled with the shaft of the bone anchor.

7. The bone anchor assembly of claim 1, wherein the extension portion of the shaft comprises a breakaway portion configured to separate from the shaft when the spinal fixation element is secured by the bone anchor assembly.

8. The bone anchor assembly of claim 1, wherein the extension portion of the shaft comprises a machine threaded portion for engaging threads on a securing element.

9. The bone anchor assembly of claim 1, further comprising a clamp element for clamping the spinal fixation element against the top surface of the seat element.

10. The bone anchor assembly of claim 9, wherein the clamp element comprises a securing mechanism for securing the spinal fixation element between clamp element and the top surface of the seat element.

11. The bone anchor assembly of claim 1, further comprising a double clamp element for clamping the spinal fixation element against the top surface of the seat element and for simultaneously clamping a different spinal fixation against an opposite side of the top surface of the seat element.

12. A bone anchor assembly for spanning a separation distance to connect laterally with a spinal fixation element, the assembly comprising:
  a bone anchor comprising:
    a shaft having:
      an engagement portion for engaging bone disposed at a distal end of the shaft,
      an extension portion disposed at a proximal end of the shaft, the extension portion comprising:
        a machine threaded portion configured to engage a securing element, and
        a detachable breakaway portion configured to separate from the shaft after when spinal fixation element is secured by the bone anchor assembly; and
      a central axis extending through the engagement portion of the shaft and the extension portion of the shaft; and
    an elliptical seat element disposed between the engagement portion of the shaft and the extension portion of the shaft, the seat element having:
      a profile flared in the direction of the proximal end of the shaft; and
      a top surface configured to be substantially flat to seat a previously inserted spinal fixation element separated from the shaft by the separation distance in a first direction and facing the proximal end of the shaft, the top surface of the seat element having a first seat distance, wherein the first seat distance is greater than or about equal to the sum of half of a cross-sectional width of the spinal fixation element, a radius of the shaft and 2 mm, wherein the first seat distance is the radial distance between the central axis of the bone anchor shaft and an outer edge of the top surface of the seat element in the first direction.

* * * * *